US00PP08130P

United States Patent [19]

Fell

[11] Patent Number: Plant 8,130

[45] Date of Patent: Feb. 2, 1993

[54] SPATHIPHYLLUM 'LEPRECHAUN'

[76] Inventor: David Fell, Hawaiian Sunshine Nursery, Hilo, Hi. 96720

[21] Appl. No.: 659,884

[22] Filed: Feb. 25, 1991

[51] Int. Cl.[5] ..... A01H 5/00

[52] U.S. Cl. ..... Plt./88.1

[58] Field of Search ..... Plt./88, 88.1

[56] References Cited

U.S. PATENT DOCUMENTS

P.P. 5,188 2/1984 Coody ..... Plt. 88

*Primary Examiner*—James R. Feyrer

*Attorney, Agent, or Firm*—Frank B. Robb

[57] ABSTRACT

A Spathiphyllum cultivar created by crossing parents which have the desired characteristics of free flowering for four inch pot production with leaf color of one parent and leaf shape and clumping habit from the other parent, the resulting plant having the desirable characteristics sought for commercial production.

1 Drawing Sheet

BACKGROUND OF THE DISCLOSURE

The object of this invention is to select parents which have certain characteristics that are thought to be desirable, crossing them to produce a cultivar which is free flowering for four inch pot production with other characteristics which are desirable and necessary for commercial acceptance.

In the nursery with which I am associated near Hilo, Haw., I have had an opportunity to observe and select plants which I believe have commercial possibilities as well as attractive characteristics.

Thus as an example in this instance, I have selected a seed parent known as 'Mini', an unpatented spathiphyllum variety in an effort to produce a larger plant, having a darker color and matte finish, hardier than the parent and having the resistance to cylindricladium as reported for 'Mini'.

The pollen parent of the plant of this application is also an unpatented variety known as 'Lechlerianum' which was chosen in the cross described because of its larger size, increased hardiness, and ability to form a denser clump.

SUMMARY OF THE VARIETY

The plant of the instant application may be described by the following characteristics which, when combined, distinguish the plant from each of the parent plants as well as other members of Araceae Spathiphyllum plant with which I am familiar.

The plant is very free breaking and dense as a mature plant.

The leaves are relatively uniform in size, lanceolate, but non-symmetrical. One side of the leaf is larger than the other. The new leaves are light green with white along the mid-rib. This coloration vanishes as the leaf matures. There is also some unstable, random variegation of the silver color. This shows up on some leaves and not on others. The leaves may be described as moderately furrowed, having moderately furrowed ribbing and moderate but conspicuous undulations between primary veins of a herringbone pattern.

The production of new plants by tissue culture in the usual controlled environment, clearly discloses the continued maintenance of the characteristics described herein.

BOTANICAL DESCRIPTION OF THE PLANT

Figure 1:
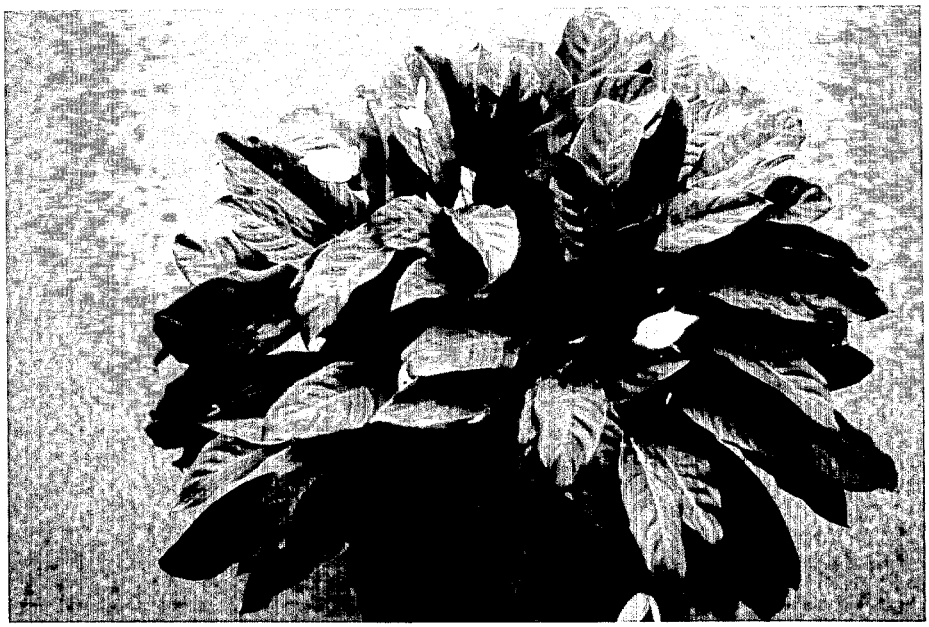

FIG. 1 of the drawing depicts in perspective a specimen of the plant at a market stage in a 10 inch pot showing the characteristic plant shape, density, uniformity of leaf size, and contrasting characteistic flowers.

Figure 2:
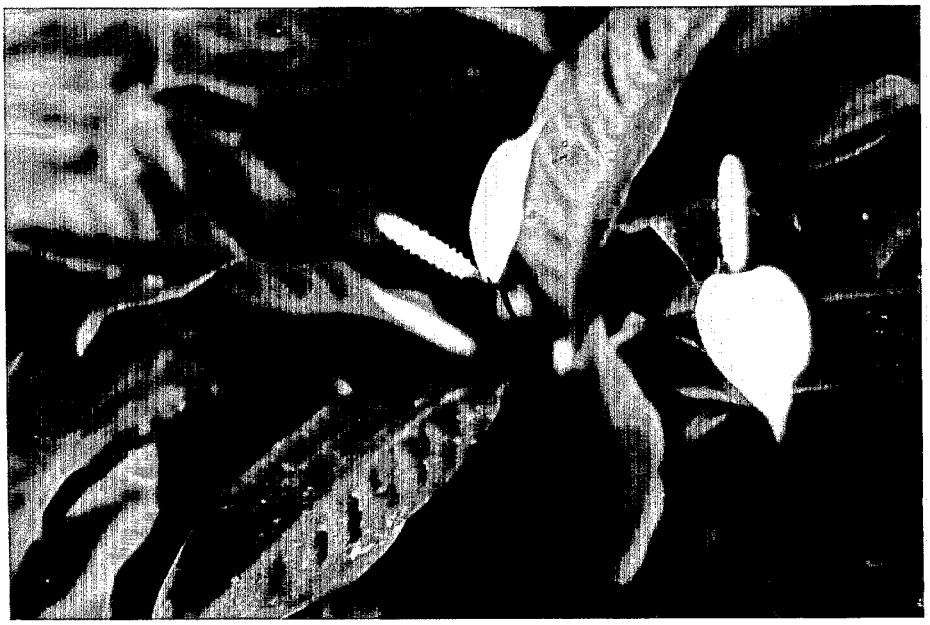

FIG. 2 of the drawing is a close-up view, disclosing the inflorescence in greater detail and depicting the unusual angle of spadix to peduncle as well as the reflexing of the spathe of the mature flower head, and leaf shape, margin, color and surface characteristics in great detail.

Color values presented in the botanical description of the plant which is set forth hereinafter, where taken from the Nickerson Color Fan by Munsell Color Co.

Color values of ordinary meaning are used were appropriate.

Detailed aspects of my new cultivar which have been established, involve the larger size of the plant than the seed parent 'Mini' and darker color of leaves with similar finish.

It appears to be lighter than the pollen parent lechlerianum also unpatented and has proven to be hardier than 'Mini'.

The free flowering habit has been established in my new plant which is denominated 'Leprechaun' for commercial presentation.

One of the advantages of my new plant is that the growth speed of the pollen plant lechlerianum has been passed on, together with the leaf shape and clumping habit.

It appears to have about the vigor of the pollen parent as well.

In summary, the plant produced has inherited many of the desirable characteristics of both parents and the details thereof are set forth in the following specific description which will make the same more clearly identifiable.

Flower:

*Blooming habit.*—Location where observations were made Apopka, Fla. 32712. Blooms — profusely. Recurrence — continuous.

Bud:

*Size.*—10 mm by 60 mm; small.

*Form.*—Long; pointed. Opening not affected by wet or hot weather.

*Color.*—When spathe first divide — white.

*Spathe.*—Smooth edge; "hood" above bud. Shape — Vaginate-lanceolate with accuminate tips. Size — small. Aspect — smooth. Odorless.

*Peduncle.*—Length — short. Aspect — smooth. Strength — erect; slender. Bud opens well. Not affected by adverse conditions. The stipes are at an oblique angle relative to the peduncles. The spathes are of lanceolate shape, have acuminate tips which reflex progressively away from the spadices as the plant matures.

Bloom:

*Size.*—30 mm by 60 mm; small; average size when fully expanded 30 mm by 60 mm.

*Borne.*—Singly; 16–20 blooms in a 10" pot.

*Form.*—When first open — flat. Performance — retains its form to the end.

*Fashion.*—Spathe with spadix.

*Number of petals under normal conditions.*—None.

*Color.*—White; slight green on the tip of the spath. Inflorescence is unusual and perhaps unique, since it does rise from petiolar sheaths of vaginate character.

Spathe: Thick; leathery. Not affected by wet or hot weather.

*Appearance.*—Inside and outside — shiny.

*Form.*—Oval.

*Persistance.*—Hang on and dry.

*Fragrance.*—None.

*Lastingness.*—On the plant — very long.

Genital organs:

*Stamens.*—Anthers — small; many. Color — white. Arrangement — regular around styles. Filaments — short. Color — white.

*Pollen.*—Color — off-white.

*Styles.*—Columnar; even. Length — short; heavy.

*Stigmas.*—Color — white.

Ovaries.—All enclosed in calyx. Seeds seldom form even when self-pollinated. To date F-2 crosses have not taken, indicating some degree of infertility.

Plant:

*Form.*—Bush.

*Growth.*—Vigorous.

*Height.*—12–18" in a 10" pot.

*Spread.*—30–36" in a 10" pot.

*Stems.*—Medium: 20–22 cm.

Foliage:

*Size.*—Small.

*Quantity.*—Abundant.

*New foliage color.*—Upper side — 7.5GY 4/4 moderate olive green. Under side — 7.5 6Y 5/7 moderate yellow green (with a silver cast).

*Shape.*—Lanceolate not symmetrical.

*Texture.*—Smooth.

*Ribs and veins.*—Prominent.

*Edge.*—Smooth.

*Leaf stem.*—Color — same as leaf.

*Under side.*—Smooth.

The leaves are relatively uniform in size, lanceolate but non symmetrical, one side of the leaf being larger than the other. The new leaves are light green with white along the mid-rib. This coloration vanishes as the leaf matures. There is also some unstable, random variegation of a silver color. This shows up on some leaves and not on others. The description might be said to provide that the leaves are of moderately furrowed ribbing and moderate but conspicuous undulations between primary veins of a herringbone pattern.

I claim:

1. A new and distinct cultivar of Spathiphyllum as herein shown and described, characterized particularly as to novelty by the larger size than the seed parent, with darker color leaves and similar finish, greater hardiness than the seed parent, free flowering production, with clumping habit and shape of leaf of the pollen parent, together with growth speed of the latter, hybrid vigor being better than both parents.

* * * * *